United States Patent [19]

Wu

[11] Patent Number: 4,701,411
[45] Date of Patent: Oct. 20, 1987

[54] BILIRUBIN-SPECIFIC ENZYME PREPARATION, ASSAY COMPOSITIONS, ANALYTICAL ELEMENTS AND METHODS USING SAME

[75] Inventor: Tai-Wing Wu, Rochester, N.Y.

[73] Assignee: Eastman Kodak Company, Rochester, N.Y.

[21] Appl. No.: 528,486

[22] Filed: Sep. 1, 1983

[51] Int. Cl.[4] .................. A61K 37/50; C12Q 1/26; C12N 9/02; C12N 11/00

[52] U.S. Cl. .................. 435/25; 435/174; 435/189; 435/805; 424/94.4; 436/97; 422/56

[58] Field of Search ............ 435/4, 25, 174, 219, 435/805, 23, 189; 424/94; 436/97; 422/56, 57

[56] References Cited

U.S. PATENT DOCUMENTS

| | | | |
|---|---|---|---|
| 4,211,844 | 7/1980 | Wu | 435/25 |
| 4,554,249 | 11/1985 | Kosaka et al. | 435/10 |
| 4,600,689 | 7/1986 | Matsui et al. | 435/25 |

FOREIGN PATENT DOCUMENTS 0061000  4/1983  Japan .................. 435/23

OTHER PUBLICATIONS

Murao and Tanaka, *Agric. Biol. Chem.*, 45(10), pp. 2383-2384 (1981).
Jacobsen and Wennberg, *Clin. Chem.*, 20(7), pp. 783-789 (1974).
Ward, Artemas, *The Encyclopedia of Food*, publ. Artemas Ward, New York, ©1923, pp. 20-22, 189 and 357.

*Primary Examiner*—Thomas G. Wiseman
*Assistant Examiner*—Elizabeth C. Weimar
*Attorney, Agent, or Firm*—J. Lanny Tucker

[57] ABSTRACT

An enzyme preparation having specific bilirubin degrading activity is described. The enzymes useful therein are obtained from various higher plant sources of the families Solanaceae, Musaceae and Liliaceae. Specific plant sources include eggplants, tomatoes and potatoes from the Solanaceae family, bananas from the Musaceae family, and onions from the Liliaceae family. Assay compositions, analytical elements and methods for use of such are also described.

22 Claims, 5 Drawing Figures

BILIRUBIN-SPECIFIC ENZYME PREPARATION, ASSAY COMPOSITIONS, ANALYTICAL ELEMENTS AND METHODS USING SAME

FIELD OF THE INVENTION

This invention relates to an enzyme preparation having specific bilirubin degrading activity. This preparation is obtained from certain higher plants, namerly from plants of the families Solanaceae, Musacease and Liliaceae. This invention also relates to the use of such preparation in assay compositions, analytical elements and methods.

BACKGROUND OF THE INVENTION

Bilirubin is a yellow substance which is formed in the blood as a result of degradation of hemoglobin, and is the principal pigment of bile manufactured in the liver. It has been estimated that approximately 200–230 milligrams of bilirubin and its derivatives are formed each day in a healthy human adult by the degradation of hemoglobin within the liver, spleen and bone marrow.

The diagnostic significance of bilirubin is well established. For example, an excessive amount of bilirubin within the human body, referred to as jaundice, is recognized as evidence of a variety of disease conditions, particularly diseases of the liver. In addition, jaundice often occurs in new born infants whose liver is slow to begin normal function. Thus, to facilitatee early diagnosis of certain disease states and/;or to actively reduce bilirubin levels, a bilirubin specific enzyme would be very useful.

Enzymes shown to be specific for bilirubin have been partially purified and characterized from certain fungi, as described in U.S. Pat. No. 4,211,844 (issued July 8, 1980 to myself) and in the literature article by Mura and Tanaka, "A New Enzyme 'Bilirubin Oxidase' Produced by *Myrothecium verrucaria* MT-1", *Agric. Biol. Chem.*, 45(10), pp. 2383-2384 (1981). However, the enzymes obtained from such sources, particularly from the mushrooms described in my patent, have rather low specific activity for bilirubin. Because of this low specific activity, larger quantities of enzymes are required to provide acceptable assay results. Furthermore, the fungi from which those enzymes are obtained are not always readily available in large quantities except at high expense.

Hence, it would be desirable to have an enzyme highly specific to degrading bilirubin and suitable for bilirubin assays, which enzyme is available from readily-available sources at relatively low cost.

SUMMARY OF THE INVENTION

The present invention provides a novel bilirubin-specific, enzyme preparation comprising an enzyme obtained from certain higher plants, namely plants of the families Solanaceae, Musaceae and Liliaceae. This enzyme is unexpectedly capable of acting specifically on bilirubin. It has been found that the specificity of this enzyme for bilirubin is up to several times higher than the specificity of the known fungal enzyme described in U.S. Pat. No. 4,211,844 noted hereinabove. Furthermore, the plants of these families, e.g., eggplants, tomatoes, potatoes, bananas and onions, are much more readily available as enzyme sources and at lower cost than mushrooms.

In accordance with the invention, a bilirubin-specific enzyme preparation comprises an enzyme derived from a plant of the group of families consisting of Solanaceae, Musacease and Liliaceae which, in the presence of a bilirubin-containing aqueous liquid, degrades bilirubin at a pH in the range of from about 6 to about 10 and temperature in the range of from about 20° to about 50° C.

This novel enzyme preparation can be used to remove bilirubin from a biological fluid, e.g. whole blood or serum, when bilirubin is present in a detrimental amount. The enzyme preparation can also be used in an assay composition for the determination of an analyte other than bilirubin in an aqueous liquid sample containing bilirubin. Such composition comprises an interactive composition and the enzyme preparation described hereinabove. The enzyme thereby degrades bilirubin and reduces its interference with the assay.

This invention also includes an analytical element for detecting an analyte (e.g. bilirubin), such element comprising the bilirubin-specific enzyme described hereinabove. In a preferred embodiment, this element includes a support and a reagent zone containing the bilirubin-specific enzyme.

Further still, this invention provides a method for the degradation of bilirubin in an aqueous liquid sample. Thus, this method comprises contacting the liquid sample with a bilirubin-specific enzyme preparation to degrade bilirubin. Such enzyme preparation contains an enzyme derived from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C.

One embodiment of this method is a method for the determination of bilirubin in an aqueous liquid sample. Such a method comprises the steps of:

(a) contacting the liquid sample with the bilirubin-specific enzyme preparation described hereinabove to interact bilirubin with the enzyme preparation and to produce a detectable change; and (b) detecting the change.

In another embodiment of the bilirubin-degrading method described above, a method for the determination of an analyte other than bilirubin in an aqueous liquid sample comprises the steps of:

(a) treating the sample with an interactive composition for the analyte to produce a detectable change;

(b) prior to or during step (a), contacting the sample with the bilirubin-specific enzyme preparation described hereinabove, thereby reducing the potential of bilirubin interference with the detectable change produced in step (a); and (c) detecting the change produced in step (a).

DETAILED DESCRIPTION OF THE INVENTION

Figure 2:
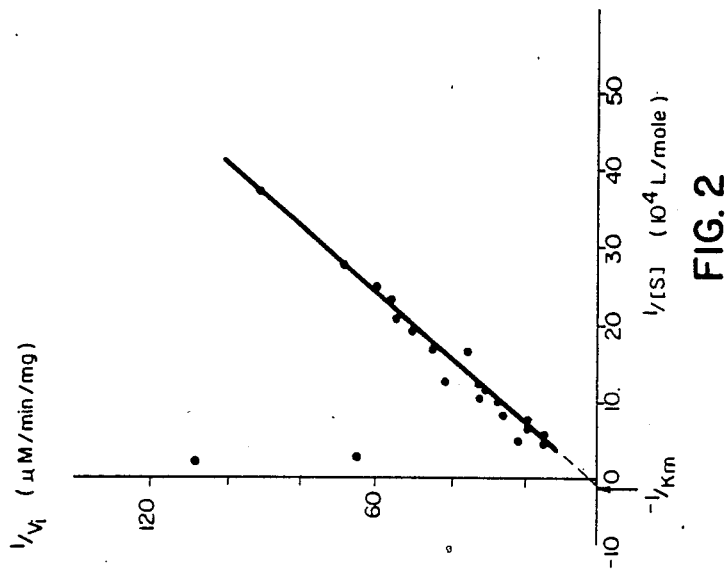
FIG. 2 is a graphical plot illustrating the kinetics of bilirubin degradation by the eggplant enzyme preparation of this invention, i.e. the inverse of initial velocity ($V_i$) in response to the change in the inverse of the concentration of bilirubin (substrate S) in the sample being assayed.

An especially valuable property of the novel enzyme preparations of this invention is their specific activity on bilirubin. Thus, when the preparation is incubated with biliverdin or hemoglobin, both of which are highly colored and chemically similar to bilirubin, no visible change occurs (see Example 4 hereinbelow.) This indicates enzyme inactivity on substances closely related to bilirubin and specificity for bilirubin.

The bilirubin-specific enzymes useful in these preparation can be extracted from plants of the families Solanaceae, Musaceae and Liliaceae. Examples of such plants of the Solanaceae family are plants from the genera Solanum, Capsicum and Lycopersicum. Useful species of such plants include, but are not limited to, eggplants (*Solanum melongena*), sweet peppers (*Capsicum grossum*), tomatoes (*Lycopersicum esculentum*) and Irish potatoes (*Solanum tuberosum*). Examples of plants of the Musaceae family are plants from the Musa genus and include, but are not limited to, bananas and related plants (*Musa paradisiaca, Musa sapientum* and *Musa acuminata*). Examples of plants of the Liliaceae family are plants from the Allium genus and include, but are not limited to, onions (*Allium cepa*), garlic (*Alium sativum*), chives (*Allium schoenoprasum*), leeks (*Allium porrum*) and wild onions (*Allium cernuum*). The enzymes which are prepared are those derived from plants of the Solanum, Musa and Allium genera such as *Solanum melongena, Musa sapientum* and *Allium cepa*. Most preferred is the enzyme extracted from eggplants.

The enzymes of interest can be extracted from the desired plants by any suitable extraction method. Two such methods are described in detail in my U.S. Pat. No. 4,211,844 noted hereinabove, the disclosure of which is incorporated herein by reference in its entirety. A specific useful extraction procedure is described hereinbelow in Examples 1, 5 and 8.

Bilirubin exhibits a characteristic absorption peak (λmax) at about 40 nanometers (nm) of the electromagnetic spectrum. When the enzyme preparation of this invention degrades bilirubin in a liquid sample under suitable pH and temperature conditions, the absorbance (or absorption density) at λmax decreases. This density decrease is a detectable change and can be monitored against a reference sample which lacks bilirubin. In this manner, an aqueous liquid sample can be assayed for bilirubin.

One use of the enzyme preparation of this invention is to degrade bilirubin in a biological fluid, e.g. whole blood, when bilirubin is present in that fluid in an excessive amount. This can be done by passing the fluid through a filter device (either implanted in a patient or ex vivo) containing the enzyme preparation. A bilirubin-binding material, e.g. albumin or a mordant, such as that described in U.S. Pat. No. 4,338,095 (issued July 6, 1982 to Wu), can be used in combination with the enzyme preparation to remove any undegraded bilirubin or the products of bilirubin degradation.

Another use of the enzyme preparation of this invention is in an analytical element and method for the determination of bilirubin in an aqueous liquid sample, such as a biological fluid (e.g. whole blood, plasma, sera, lymph, bile, urine, spinal fluid, sputum, sweat and the like as well as stool secretions of humans or animals).

The method comprises:

(a) contacting an aqueous liquid sample with the bilirubin-specific enzyme preparation at a pH and temperature effective for the enzyme preparation to interact with bilirubin and produce a detectable change corresponding to the presence and/or concentration of bilirubin; and (b) detecing such a change.

Still another use of the enzyme preparation of this invention can be used to reduce bilirubin interference in assays for analytes other than bilirubin. Such assays are usually achieved with assay compositions, elements and methods using interactive compositions which, when they interact with the analyte, produce a detectable changee of some type (e.g. colorimetric, potentiometric, etc.). Any suitable interactive composition can be used with the enzyme preparation of this invention. Examples of interactive composition include enzyme-linked hydrogen peroxide detection systems, enzyme-linked NAD-NADH detection systems, redox reactions, hydrolysis reactions and others known in the clinical chemistry art.

The interactive composition useful in an assay of an analyte other than bilirubin can be any composition capable of physical, electrical, chemical or other interaction with the analyte of interest leading to a detectable change, for example, an absorbance shift or a change in absorption density, which can be related to the presence and/or amount of the analyte.

In this embodiment of reducing bilirubin interferences, a liquid sample is treated with bilirubin-specific enzyme preparation before, or while, the sample containing the analyte is treated with the interactive composition. The bilirubin-specific enzyme preparation reduces the potential of bilirubin interference in the assay for the analyte.

The enzyme preparations of this invention are effective to interact with bilirubin within wide pH and temperature ranges, e.g. from about 6 to about 10 and from about 20° to about 50° C., respectively. However, they are particularly effective in pH and temperature ranges of from about 6.5 to about 8.5, and from about 25° to about 45° C., and most effective in the pH and temperature ranges of from about 7.0 to about 7.5, and from about 30° to about 37° C., respectively.

Although it is optional, it is preferred to use a buffer with the enzyme preparation of this invention. Together, the enzyme preparation and the buffer can be used as an assay composition. A buffer is present in such a composition to maintain the pH within the pH range effective for bilirubin degradation. Phosphates, such as sodium phosphate, are particularly suitable. However, a variety of other useful buffers (e.g. borates) are known.

The amount of the enzyme preparation useful in the practice of this invention depends upon the bilirubin concentration of the liquid sample to be assayed. Generally, in solution assays, the enzyme preparation is used in an amount in the range of from about 0.01 to about 0.2, and preferably in the range of from about 0.02 to about 0.1, milligrams per deciliter. This assumes that each mg of enzyme preparation has the minimum activity level for bilirubin of at least 0.02 micromoles of bilirubin per minute as determined in an aqueous liquid at a pH of about 7.3 and a temperature of about 37° C. When using an enzyme preparation of higher activity, proportionately smaller amounts of the enzyme preparations can be used.

When an enzyme preparation of this invention is employed to eliminate or reduce bilirubin as an interferent in an assay, the interactive composition which is employed must itself be non-interfering with respect to the enzyme preparation. For example, if the analyte is to be detected by use of an interactive composition containing a hydrogen peroxide detection composition, it would clearly be inappropriate to use an enzyme preparation which itself generates hydrogen peroxide. Because the enzyme preparation of the invention can be used to degrade bilirubin without generation of hydrogen peroxide, this particular problem is avoided.

The detectable change produced by the methods of this invention can be detected by a wide variety of means. For example, the methods can employ a suitable detection capable of detecting a change in absorption density, a change in fluorescent or radioactive emission or a shift in the absorbance of a characteristic $\mu$max.

The enzyme preparation and methods of this invention are adaptable to both solution (i.e. "wet chemistry") and dry elements (i.e. "dry chemistry") assays. In solution assays, the assay is carried out entirely in a liquid medium, and the enzyme preparation or assay composition containing it is employed as a liquid reagent. In such case, the enzyme preparation or assay composition is mixed with the aqueous liquid sample to be assayed at the desired pH and temperature. This solution assay technique is described in more detail hereinbelow in Example 2.

When employed in "dry chemistry" elements, the enzyme preparation or assay composition can be incorporated into a suitable location of a suitable analytical element by imbibition, impregnation, coating or other suitable techniques. For example, the preparation can be incorporated into a reagent layer of a dip-and-read fibrous test strip or a fibrous or non-fibrous multilayer element, such as that described in U.S. Pat. No. 3,992,158 (issued Nov. 16, 1976 to Przybylowicz et al), the disclosure of which is incorporated herein by reference in its entirety. The methods of this invention are then practiced by contacting (e.g. spotting) the element with the aqueous liquid sample to be assayed. Any detectable change which then occurs within the element is measured with appropriate apparatus. The enzyme preparation or assay composition is present in such elements as a dried residue (e.g. a freeze-dried powder or dried residue of a coating composition).

When used in dry element assays, the bilirubin-specific enzyme preparation is generally present in an amount in the range of from about 40 to about 40 U/m$^2$, and preferably in an amount in the range of from about 50 to about 200 U/m$^2$.

The analytical elements of this invention generally have at least one reagent zone containing the enzyme preparation or assay composition of this invention. These zones can be self-supporting (i.e. composed of materials rigid enough to maintain their integrity), but preferably they are carried on a support. Such a support can be of any suitable dimensionally stable, and preferably, transparent (i.e. radiation transmissive) material which transmits electromagnetic radiation of a wavelength between about 200 and 900 nm. Useful support materials include polystyrenes, polyesters (e.g. poly(ethylene terephthalate)), polycarbonates, cellulose esters, etc. The element can have a plurality of zones, some or all containing reagents. These zones are in fluid contact with each other, meaning that fluids can pass between superposed regions of adjacent zones. States in another manner, fluid contact refers to the ability to transport components of a fluid between the zones in fluid contact. Preferably, the zones are separate coated layers, although one or more zones can be in a single layer of an element. Dry element formats and materials to make such are known in the art and described, for example, in U.S. Pat. No. 3,992,158 noted hereinabove; as well as in U.S. Pat. Nos. 4,042,335 (issued Aug. 16, 1977 to Clement); 4,144,306 (issued Mar. 13, 1979 to Figueras); 4,132,528 (issued Jan. 2, 1979 to Eikenberry et al); 4,050,898 (issued Sept. 27, 1977 to Goffe et al); 4,258,001 (issued Mar. 24, 1981 to Pierce et al); and Reissue 30,267 (reissued May 6, 1980 to Bruschi) and disclosures of which are incorporated herein in their entirety.

Any of the reagent zones of these elements can also act as a spreading zone. Additionally, or alternatively, the element can have one or more separate spreading zones. A spreading zone is typically a layer which can accept a liquid sample. When the liquid sample is applied directly to the layer or provided to it from a layer or layers in fluid contact with it, the solvent or dispersion medium of the sample is distributed such that a uniform apparent concentration of the sample is provided at the surface of the spreading layer facing the adjacent reagent layer. Useful materials for preparing spreading zones are described, for example, in U.S. Pat. Nos. 3,992,158 and 4,258,001, noted hereinabove; and 4,292,272 (issued Sept. 29, 1981 to Kitajima et al); and U.K. Patent Application 2,052,057 (published Jan. 21, 1981). The spreading zone, for example, can be composed of either fibrous or non-fibrous materials, or both. Preferably, the spreading zone is an isotropically porous spreading layer as described in U.S. Pat. No. 3,992,158, noted hereinabove.

One or more zones (e.g. reagent, spreading, subbing, barrier or registration) of the elements of this invention can contain a variety of one or more other desirable, but optional components, including surfactants, enzyme activators, binders (generally hydrophilic natural or synthetic colloids or polymers), hardeners, dyes, solvents, etc. These componenets are present in amounts known in the clinical chemistry art.

A variety of different elements, depending on the method of assay, can be prepared in accordance with the present invention. Elements can be configured in a variety of forms, including elongated tapes of any desired width, sheets or smaller chips.

The analytical method of this invention can be manual or automated. In general, the amount of bilirubin or other analyte in a liquid is determined by taking the element from a supply roll, chip packet or other source and physically contacting it with a sample of the liquid. Such contact can be accomplished in any suitable manner, e.g. dipping or immersing the element into the sample or, preferably, by spotting the element by hand or machine with a drop of the sample by pipette or another suitable dispensing means.

After sample application, the element is exposed to any conditioning, such as incubation, heating or the like, that may be desirable to quicken or otherwise facilitate obtaining any test result.

The analyte or bilirubin, if present, then reacts and produces a detectable change which is quantifiable by passing the element through a zone in which suitable apparatus for detection is provided.

Suitable detection means include the use of reflection or transmissive colorimetric spectrophotometry, fluorescene spectrophotometry, radiometry, chemiluminescene, enzyme labeling, measurement of enthalphy changes and the like.

The examples below further illustrate the invention. The following information is common to the examples.

Protein concentration was determined by the method of Warburg & Christian (*Biochem. Z.*, 310:384, 1941) using a ratio of absorbances measured at 280 and 260 nm. Unless otherwise stated, all enzyme preparation extraction steps were carried out at 0°–4° and all chemicals were reagent grade and were obtained from Eastman Kodak Co., Rochester, New York. Bilirubin used was a product of Sigma Chemical Co., St. Louis, Missouri. A bilirubin (unconjugated form) stock solution (100 mg/mL) was prepared by dissolving the weighed, solid material (prewet with about 100 μL of 0.1N NaOH) in 0.05M sodium phosphate buffer (pH 7.45) in a 100 mL flask. This solution was kept at 0°–4° C. under a nitrogen-enriched atmosphere. A molar absorptivity of $55 \times 10^3$ L/mole/cm at 440 nm was used for bilirubin (see method of Jacobsen & Wennberg, *Clin. Chem.*, 20:783, 1974). Just prior to use, the bilirubin stock solution was diluted with 0.05M of the sodium phosphate buffer.

Bilirubin-containing solutions, buffered as stated above were incubated with an aliquot of the enzyme preparation and the decrease in absorption density at λmax (440 nm) was monitored against a reference solution of identical composition but without bilirubin. The final volume of each reaction mixture was 1.01 mL. All assays were monitored at 22°–25° C. on a Perkin-Elmer Model 576 Spectrophotometer at 440 nm, unless otherwise stated.

EXAMPLE 1

Extraction of Enzyme from Eggplants of the Solanaceae Family

Eggplants were rinsed with distilled water, sliced and added to 3–4 volumes of ice-chilled 0.05M sodium phosphate buffer (pH 7.45). The eggplant tissues were then homogenized with conventional blender with 10–12 separate bursts, each burst lasting 10–15 seconds, interspersed with 30-second periods of ice-bath chilling. The resulting homogenate was filtered through 3 layers of cheesecloth. The brown filtrate was then centrifuged in a Beckman JC-21 centrifuge at 9,000 xg and 4° C. for 20 minutes. The resulting pellet, exhibiting negligible bilirubin-specific activity, was discarded, and the supernatant was treated with an equal volume of dry ice-chilled acetone. The mixture was stirred in an ice bath containing both ordinary and dry ice. When the temperature of the solution reached −10° C., stirring was stopped and the solution was left to stand at 4° C. for 20 minutes before it was centrifuged at 9,000 xg and 4° C. for 30 minutes. The resulting pellets were resuspended in 1–2 volumes of 0.05M sodium phosphate buffer (pH 7.45) and diluted with ice-chilled ethanol (1:1, V/V). The resulting mixture was centrifuged at 8,000 xg and 4° C. for 15 minutes, whereupon it separated into three phases: (1) an upper clear liquid which exhibited most of the enzyme activity; (2) a cloudy interface exhibiting some activity; and (3) a pellet at the bottom of the centrifuge tube exhibiting no activity. Two repeated extractions of the cloudy interface using ethanol resulted in the release of more enzyme activity into the upper clear phase. The clear upper phase was dried down and resuspended in the buffer. It exhibited full enzyme activity for degrading bilirubin. Results obtained from enzyme extracted by this procedure from three separate batches of eggplant starting material are shown in Table I below.

TABLE I

| Purification Step | Eggplant Batch* | PROTEIN | | | ACTIVITY | | |
|---|---|---|---|---|---|---|---|
| | | mg/mL | Total mg | % Recovery of Protein | Specific Activity** | Total Units | % Recovery of Activity |
| Crude Homogenate | 1 | 12.4 | 9293 | 100 | 0.0186 | 173.2 | 100 |
| | 2 | 9.4 | 7065 | 100 | 0.0245 | 173.1 | 100 |
| | 3 | 15.9 | 11888 | 100 | 0.0156 | 185.5 | 100 |
| Acetone Precipitation | 1 | 7.1 | 1065 | 11.5 | 0.2186 | 232.9 | 134.4 |
| Ethanol Extraction | 1 | 1.5 | 38.3 | 0.41 | 0.439 | 16.8 | 9.7 |
| | 2 | 1.53 | 38 | 0.54 | 0.483 | 18.5 | 10.6 |
| | 3 | 2.3 | 56.5 | 0.48 | 0.370 | 20.9 | 11.3 |

*The acetone-treated material was not assayed from batches 2 and 3. Those batches were carried directly to ethanol extraction.
**Activity was determined by calculating the number of μmoles of bilirubin degraded per minute per mg. based on the rate of change at $A_{440}$ using a molar extinction coefficient of $59 \times 10^3$ at pH 7.45 and 25° C. A 2 mg/mL bilirubin solution was used in activity tests.

The enzyme was solubilized in each of several alcohols (e.g. ethanol, propanol or butanol) to form a clear solution that was stable for storage over several days at 0°–4° C.

EXAMPLE 2

Figure 1:
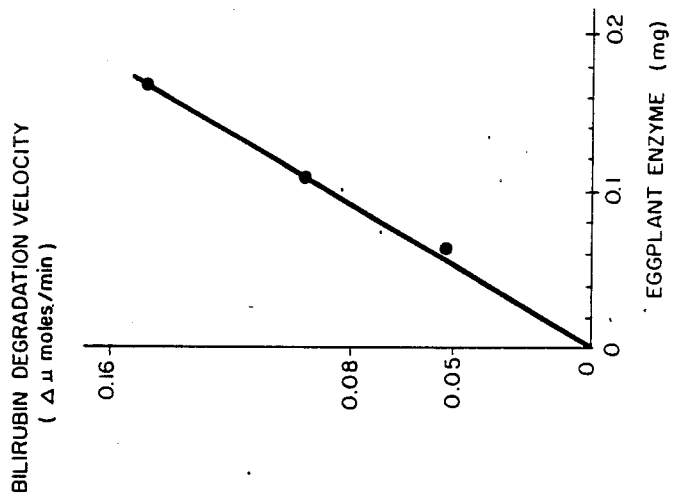
FIG. 1 is a graphical plot illustrating the change in bilirubin degradation velocity in response to the change in amount of the bilirubin-specific eggplant enzyme preparation of this invention.

Billirubin Degradation in Solution Assay as a Function of Eggplant Enzyme Concentration Different amounts of the enzyme extract obtained from eggplants by the procedure described in Example 1 were added to separate liquid samples containing 2 mg/dL bilirubin freshly prepared in 0.05 M sodium phosphate buffer (pH 7.45) at 25° C. The decrease in absorption density at λmax (440 nm) was monitored against a reference of identical composition but without bilirubin using a conventional spectrophotometer. As illustrated in FIG. 1, the initial velocity of the degradation reaction varies linearly with the amount of enzyme used up to about 0.17 mg protein. At higher amounts, linearity was not observed.

EXAMPLE 3

Bilirubin Degradation in Solution Assay as a Function of Bilirubin Concentration An aliquot containing 0.09 mg of eggplant enzyme preparation was added to bilirubin-containing liquid samples having concentrations of bilirubin ranging from $2.8 \times 10^{-6}$ to $2 \times 10^{-5}$ moles/L. Test conditions were the same as those described in Example 2. As illustrated in FIG. 2, the apparent extrapolated Michaelis Constant, Km, of the eggplant bilirubin-specific enzyme is about $1 \times 10^{-4}M$ (i.e., 5.8 mg/dL) (see Lineweaver & Burk, J.A.C.S., 56, p. 658, 1934).

EXAMPLE 4

Bilirubin Specificity of Enzyme Preparation

This example illustrates the specificity of the eggplant enzyme preparation of this invention for bilirubin.

In the normal metabolism of heme in mammals, hemoglobin and biliverdin are known precursors of bilirubin. Assays were carried out in the following manner to see if the enzyme preparation prepared in Example 1 would show any activity toward hemoglobin or biliverdin.

The eggplant enzyme preparation of Example 1 was added to two solutions of hemoglobin (0.5 and 1.4 g/dL, respectively) and to two solutions of biliverdin (0.9 and 5 mg/dL, respectively) to achieve a final enzyme concentration of about 1 mg/dL. Repetitive spectral scans were made on each solution for a period of 60 minutes. The hemoglobin solutions were scanned at 420 (λmax), 540 and 576 nm; and the biliverdin solutions were scanned at 380 (λmax) and 670 nm.

In each of the spectral scans, it was observed that the λmax was unchanged and that no change in absorption density occurred for periods of time up to one hour. These results suggest that the enzyme preparation did not show any specificity for hemoglobin or biliverdin.

EXAMPLE 5

Extraction of Enzyme from Bananas of the Musaceae Family

The pulp of half of one banana was homogenized in five volumes of ice-chilled 0.05M sodium phosphate buffer (pH 7.45), filtered through cheesecloth and centrifuged in a manner described for the extraction of eggplants in Example 1. The supernatant was immediately frozen at $-5°$ C. until its use.

EXAMPLE 6

Figures 3, 4:
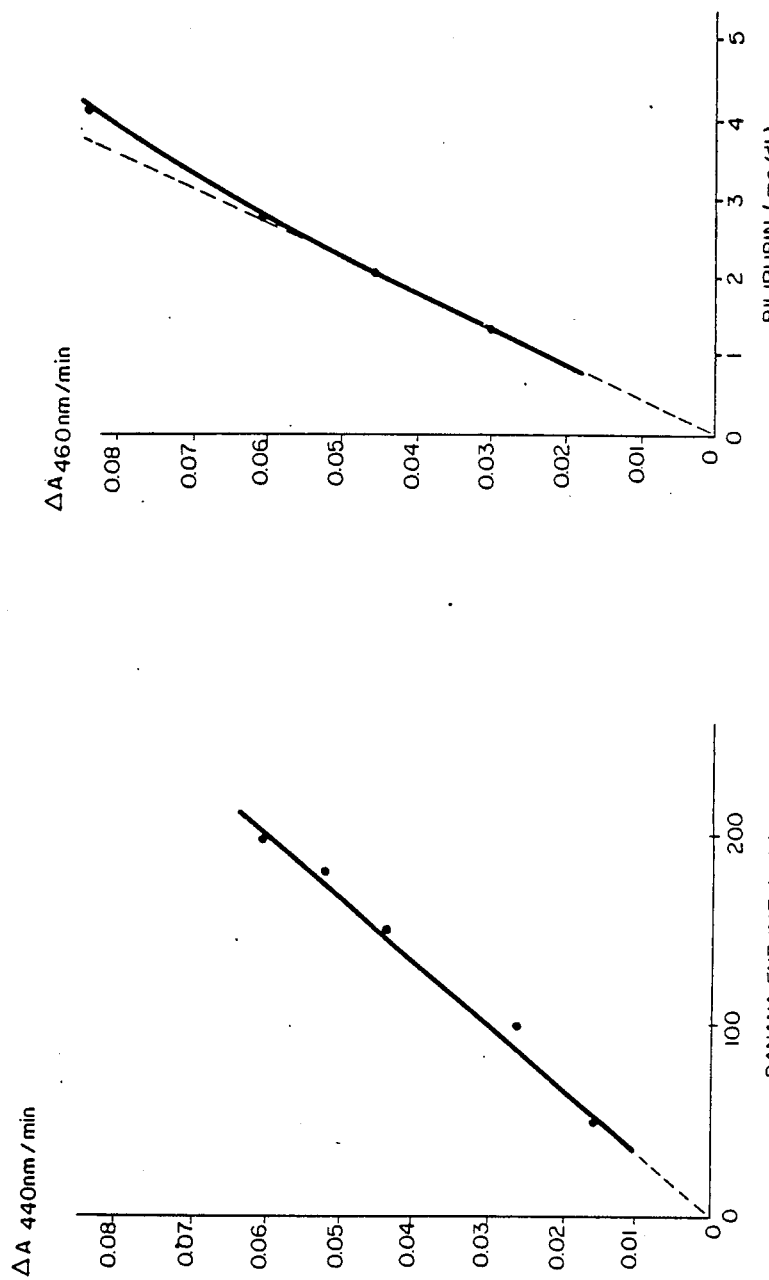
FIG. 3 is a graphical plot illustrating the change in bilirubin absorbance at λmax (440 nm) in response to the change in amount of the bilirubin-specific banana enzyme preparation of this invention.
FIG. 4 is a graphical plot illustrating the kinetics of bilirubin degradation by the banana enzyme preparation of this invention in response to the change in amount of bilirubin in the sample being assayed.

Bilirubin Degradation in Solution Assay as a Function of Banana Enzyme Concentration Different amounts of the crude enzyme extract obtained from bananas by the procedure described in Example 5 were added to separate liquid samples containing 2.74 mg/dL bilirubin freshly prepared in 0.05M sodium phosphate bufer (pH 7.45) at 25° C. The decrease in absorption density at λmax (460 nm) was monitored against a reference of identical composition but without bilirubin using a conventional spectrophotometer. As illustrated in FIG. 3, the initial velocity of the degradation reaction varies linearly with the amount of enzyme extract used up to about 200 μL (0.43 μg protein/μL).

EXAMPLE 7

Bilirubin Degradation in Solution Assays as a Function of Bilirubin Concentration A 200 μL aliquot containing about 86 μg of crude banana enzyme was added to bilirubin-containing liquid samples having a bilirubin concentrations ranging from none to about 4 mg/dL. Test conditions were the same as those described in Example 6. As illustrated in FIG. 4, the initial velocity of the crude enzyme preparation varies linearly with substrate concentration.

EXAMPLE 8

Extraction of Enzyme from Onions of the Lilaceae Family

An onion was frozen at $-70°$ C. and subsequently thawed. The first 2 or 3 layers were peeled off and the remainder was sliced, minced, homogenized with five volumes of ice-chilled 0.05M sodium phosphate buffer (pH 7), filtered through cheesecloth and centrifuged in a manner described for the extraction of eggplants in Example 1. The supernatant was separated into 5 mL aliquots and stored at 0°-4° C. until its use.

EXAMPLE 9

Figure 5:
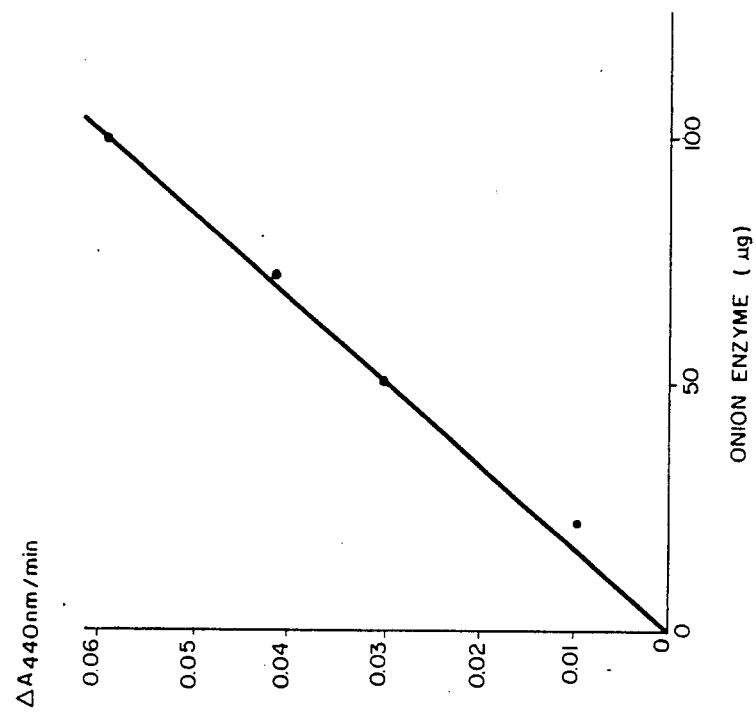
FIG. 5 is a graphical plot illustrating the change in bilirubin absorbance at λmax (440 mm) in response to the change in amount of the bilirubin-specific onion enzyme preparation of this invention.

Bilirubin Degradation in Solution Assay as a Function of Onion Enzyme Concentration Different amounts of the enzyme extract obtained from onions by the procedure described in Example 8 were added to separate liquid samples containing 2 mg/dL bilirubin freshly prepared in 0.05M sodium phosphate buffer (pH 7) at 25° C. The decrease in absorption density at λmax (440 nm) was monitored against a reference of identical composition but without bilirubin using a conventional spectrophotometer. As illustrated in FIG. 5, the initial velocity of the degradation reaction varies linearly with the amount of enzyme extract used up to about 100 μg protein.

The invention has been described in detail with particular reference to preferred embodiments thereof, but it will be understood that variations and modifications can be effected within the spirit and scope of the invention.

I claim:

1. A bilirubin-specific enzyme preparation comprising an enzyme isolated from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C. without generation of hydrogen peroxide.

2. The preparation of claim 1 wherein said enzyme is isolated from a plant of the Solanum, Capsicum or Lycopersicum genera of the family Solanaceae.

3. The preparation of claim 2 wherein said enzyme is isolated from eggplants.

4. The preparation of claim 1 wherein said enzyme is isolated from a plant of the Musa genus of the family Musaceae.

5. The preparation of claim 4 wherein said enzyme is isolated from bananas.

6. The preparation of claim 1 wherein said enzyme is isolated from a plant of the Allium genus of the family Liliaceae.

7. The preparation of claim 6 wherein said enzyme is isolated from onions.

8. An assay composition for the determination of an analyte other than bilirubin in an aqueous liquid sample in which bilirubin is an interferent for said determination, said composition comprising an interactive composition for said analyte and a bilirubin-specific enzyme preparation comprising an enzyme derived from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C. without generation of hydrogen peroxide and reduces bilirubin interference with said assay.

9. The assay composition of claim 8 comprising a buffer.

10. An analytical element for detecting an analyte, said element comrpising a self-supporting reagent zone containing a bilirubin-specific enzyme isolated from a plant of the group of families consisting of Solanaceae, Musaceae and Liliaceae which, in the presence of a bilirubin-containing aqueous liquid, degrades bilirubin at a pH in the range of from about 6 to about 10 and a tempera- ture in the range of from about 20° to about 50° C. without generation of hydrogen peroxide.

11. A dry analytical element for the assay of an aqueous liquid, said element including a support and a reagent zone containing a bilirubin-specific enzyme derived from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C. without generation of hydrogen peroxide.

12. The element of claim 11 wherein said enzyme is present in an amount of from about 40 to about 400 $U/m^2$.

13. The dry element of claim 11 wherein said enzyme is derived from a plant of the Solanum, Capsicum or Lycopersicum genera of the family Solanaceae.

14. The dry element of claim 13 wherein said enzyme is derived from eggplants.

15. A method for the degradation of bilirubin in an aqueous liquid sample, said method comprising contacting said liquid sample with a bilirubin-specific enzyme preparation to degrade bilirubin, said enzyme preparation containing an enzyme isolated from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C. without generation of hydrogen peroxide.

16. The method of claim 15 wherein said aqueous liquid is whole blood.

17. A method for the determination of bilirubin in an aqueous liquid sample, said method comprising the steps of:
(a) contacting said liquid sample with a bilirubin-specific enzyme preparation to interact bilirubin with said enzyme preparation and to produce a detectable change, said enzyme preparation containing an enzyme derived from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C. without generation of hydrogen peroxide; and
(b) detecting said change.

18. A method for the determination of bilirubin in an aqueous liquid sample, said method comprising the steps of:
(a) contacting said liquid sample with an analytical element containing a bilirubin-specific enzyme to interact bilirubin with said enzyme and to produce a detectable change, said element including a support and a reagent zone containing said bilirubin-specific enzyme which is derived from a plant of the group of families consisting of Solanaceae, Musaceae and Liliaceae and which, in the presence of a bilirubin-containing aqueous liquid, degrades bilirubin at a pH in the range of from about 6 to about 10 and a temperature in the range of from about 20° to about 50° C. without generation of hydrogen peroxide; and
(b) detecting said change.

19. The method of claim 18 wherein said detectable change is a change in the absorption density of bilirubin.

20. The method of claim 18 wherein said enzyme is derived from a plant of the Solanum, Capsicum or Lycopersicum genera of the family Solanaceae.

21. The method of claim 20 wherein said enzyme is derived from eggplants.

22. A method for the determination of an analyte other than bilirubin in an aqueous liquid sample in which bilirubin is an interferent for said determination, said method comprising the steps of:
(a) treating said sample with an interactive composition for said analyte to produce a detectable change;
(b) prior to or during step (a), contacting said sample with a bilirubin-specific enzyme preparation containing an enzyme derived from a plant of the group of families consisting of Solanaceae, Musaceae and Liliaceae which, in the presence of a bilirubin-containing aqueous liquid, degrades bilirubin at a pH in the range of from about 6 to about 10 and a temperature in the range of from about 20° to about 50° C. without generation of hydrogen peroxide, thereby reducing the potential of bilirubin interference with said detectable change produced in step (a); and
(c) detecting said change produced in step (a).

* * * * *